(12) United States Patent
Michishita et al.

(10) Patent No.: US 10,640,805 B2
(45) Date of Patent: May 5, 2020

(54) REAGENT FOR PROTHROMBIN TIME MEASUREMENT, METHOD FOR PRODUCTION THEREOF, AND METHOD FOR MEASUREMENT OF PROTHROMBIN TIME

(71) Applicant: SYSMEX CORPORATION, Kobe-shi, Hyogo (JP)

(72) Inventors: Masato Michishita, Kobe (JP); Takahiko Bando, Kobe (JP); Yusuke Tanaka, Kobe (JP); Kiyoko Kohama, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 203 days.

(21) Appl. No.: 15/472,545

(22) Filed: Mar. 29, 2017

(65) Prior Publication Data

US 2017/0283853 A1 Oct. 5, 2017

(30) Foreign Application Priority Data

Mar. 30, 2016 (JP) ................................. 2016-067983

(51) Int. Cl.
*C12Q 1/56* (2006.01)
*A61K 9/127* (2006.01)
*G01N 33/52* (2006.01)
*G01N 33/86* (2006.01)

(52) U.S. Cl.
CPC ................ *C12Q 1/56* (2013.01); *A61K 9/127* (2013.01); *G01N 33/52* (2013.01); *G01N 33/86* (2013.01); *G01N 2333/7454* (2013.01); *G01N 2333/974* (2013.01)

(58) Field of Classification Search
None
See application file for complete search history.

(56) References Cited

U.S. PATENT DOCUMENTS

| | | | |
|---|---|---|---|
| 6,100,072 A * | 8/2000 | Brucato | C07K 14/70596 435/5 |
| 6,203,816 B1 | 3/2001 | Brown | |
| 2004/0086953 A1 | 5/2004 | Jenny et al. | |
| 2008/0241941 A1* | 10/2008 | Okuda | A01K 67/0337 436/69 |

FOREIGN PATENT DOCUMENTS

| | | |
|---|---|---|
| JP | 6-38797 A | 2/1994 |
| JP | H6-502649 A | 3/1994 |
| JP | 11-225760 A | 8/1999 |
| JP | H11-514101 A | 11/1999 |
| JP | 2002-303632 A | 10/2002 |
| JP | 2004-157122 A | 6/2004 |
| JP | 2008-241621 A | 10/2008 |
| WO | 92/08479 A1 | 5/1992 |
| WO | 94/07515 A1 | 4/1994 |
| WO | 98/48283 A1 | 10/1998 |

OTHER PUBLICATIONS

The Japanese Office Action dated Oct. 23, 2019 in a counterpart Japanese patent application No. 2016-067983.

* cited by examiner

*Primary Examiner* — Marsha Tsay
(74) *Attorney, Agent, or Firm* — Sughrue Mion, PLLC

(57) ABSTRACT

Disclosed is a reagent for prothrombin time measurement, containing a tissue factor and a surfactant, wherein the value of formula (I), which is represented by (surfactant amount (μmol))/(total protein amount (μg)), is 0.013 to 0.05 μmol/μg.

10 Claims, 1 Drawing Sheet

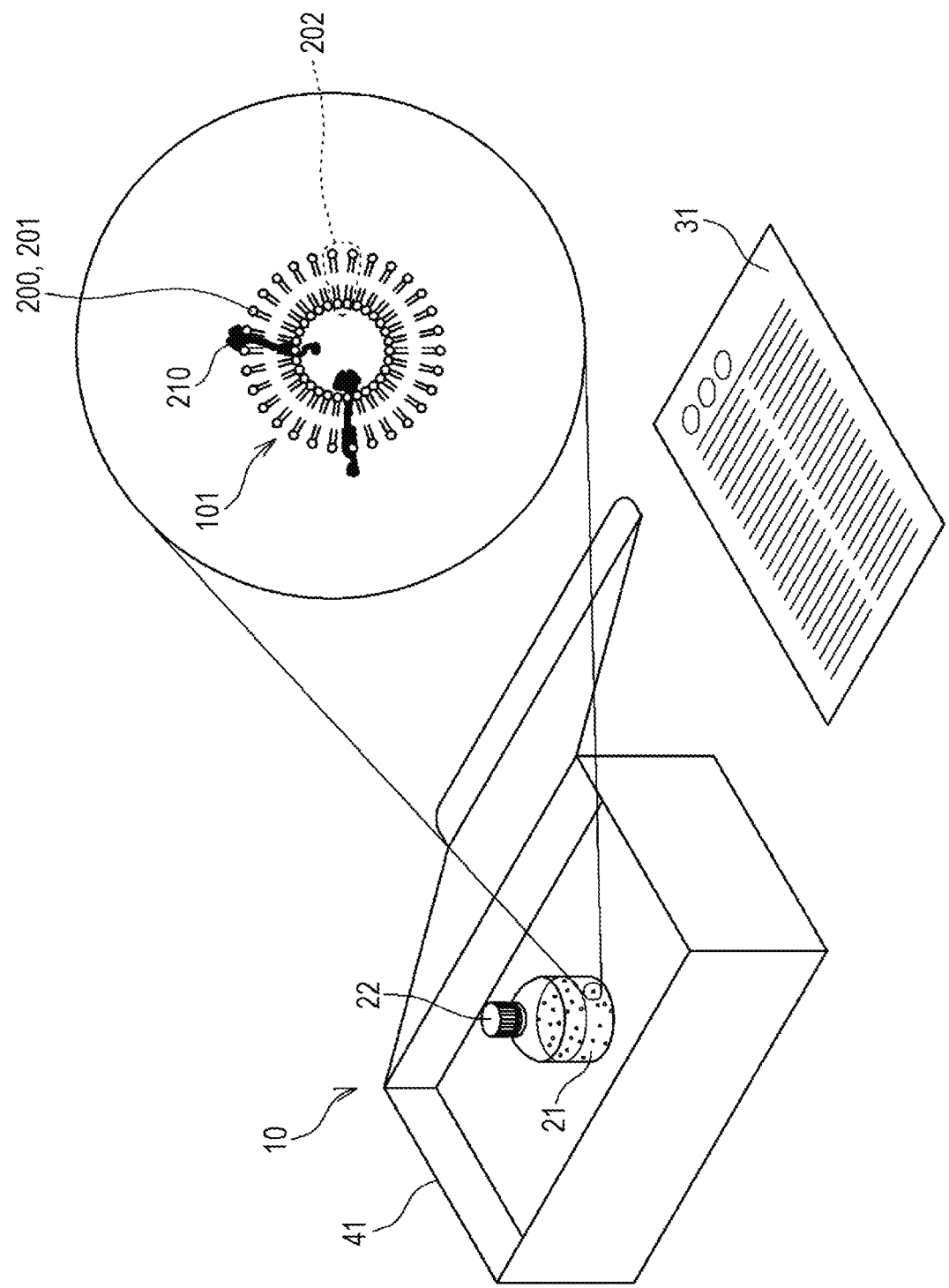

REAGENT FOR PROTHROMBIN TIME MEASUREMENT, METHOD FOR PRODUCTION THEREOF, AND METHOD FOR MEASUREMENT OF PROTHROMBIN TIME

CROSS REFERENCE TO RELATED APPLICATIONS

This application claims priority from prior Japanese Patent Application No. 2016-067983, filed on Mar. 30, 2016, entitled "REAGENT FOR PROTHROMBIN TIME MEASUREMENT, METHOD FOR PRODUCTION THEREOF, AND METHOD FOR MEASUREMENT OF PROTHROMBIN TIME", the entire contents of which are incorporated herein by reference.

TECHNICAL FIELD

The present invention relates to a reagent for prothrombin time measurement, a method for production thereof, and a method for measurement of prothrombin time.

BACKGROUND

Reagents for prothrombin time measurement are produced, for example, by mixing a tissue factor, a phospholipid, and a buffer solution containing a surfactant, and removing the surfactant from the resulting mixture (see, for example, U.S. 2004/086953 A). These reagents are usually stored in a freeze-dried state, for storage, transport, and others. Freeze-dried reagents for prothrombin time measurement are utilized in a state of being re-dissolved in an appropriate solvent when used.

However, reagents for prothrombin time measurement containing a tissue factor may cause variations in measurements of prothrombin time before and after freeze drying of the reagent.

The present invention provides a reagent for prothrombin time measurement that can control variations in measurements of prothrombin time before and after freeze drying of the reagent, a method for production thereof, and a method for measurement of prothrombin time.

SUMMARY OF THE INVENTION

The scope of the present invention is defined solely by the appended claims, and is not affected to any degree by the statements within this summary.

A first aspect of the present invention encompasses a reagent for prothrombin time measurement, containing a tissue factor and a surfactant, wherein the value of formula (I), which is represented by (surfactant amount ($\mu$mol))/(total protein amount ($\mu$g)), is 0.013 to 0.05 $\mu$mol/$\mu$g.

A second aspect of the present invention encompasses a method for a reagent for prothrombin time measurement, including a step of freeze-drying an aqueous solution containing a tissue factor and a surfactant, wherein the value of formula (I) is 0.013 to 0.05 $\mu$mol/$\mu$g, thereby to obtain a lyophilizate.

A third aspect of the present invention encompasses a method for measuring prothrombin time, including steps of: (a) mixing the above-described reagent for prothrombin time measurement with a sample of blood, thereby to obtain a measurement sample, and (b) measuring the prothrombin time of the measurement sample.

BRIEF DESCRIPTION OF THE DRAWING

FIG. 1 is a schematic view illustrating the construction of a reagent kit.

DETAILED DESCRIPTION OF THE PREFERRED EMBODIMENTS

1. Reagents for Prothrombin Time Measurement

A reagent for prothrombin time measurement according to an embodiment of the present invention (hereinafter referred to simply as a "reagent") contains a tissue factor and a surfactant. The reagent according to an embodiment of the present invention is one for measuring prothrombin time, which is on the basis of the activation mechanism of extrinsic coagulation in which a tissue factor is involved, in accordance with the measurement principle known in the art. In the reagent according to an embodiment of the present invention, the value of formula (I), which is represented by (surfactant amount ($\mu$mol))/(total protein amount ($\mu$g)), is 0.013 to 0.05 $\mu$mol/$\mu$g.

In formula (I), the "surfactant amount ($\mu$mol)" refers to the content of the surfactant in a reagent according to an embodiment of the present invention. The "total protein amount ($\mu$g)" refers to the content of total protein in the reagent. The "total protein" refers to the total of the tissue factor described below and contaminating proteins derived from an animal source for the tissue factor.

For reagents for prothrombin time measurement, variations in measurements of prothrombin time before and after freeze drying of the reagent are thought to result from the following mechanism. A conventional reagent usually contains a tissue factor, a phospholipid, a surfactant, and contaminating proteins that are derived from an animal source for the tissue factor and that are inevitably mixed into the reagent. In consequence, before the reagent is freeze-dried, most of the surfactant usually associates with the tissue factor and the contaminating proteins, thereby resulting in the formation of micelles. On the other hand, part of the surfactant does not associate with the tissue factor and the contaminating proteins, and forms micelles composed only of the surfactant. When such a conventional reagent is freeze-dried and the lyophilizate is then re-dissolved in a solvent, however, it is thought that part of the surfactant that has not associated with the tissue factor and the contaminating proteins associates with the phospholipid, thereby preventing the phospholipid from exerting its intrinsic function. For this reason, the use of a conventional reagent causes variations in measurements of prothrombin time before and after freeze drying of the reagent.

In contrast, in a reagent according to an embodiment of the present invention, the surfactant amount is adjusted relative to the total protein amount, so that the value of formula (I) will be 0.013 to 0.05 $\mu$mol/$\mu$g. Therefore, since a reagent according to an embodiment of the present invention has a reduced amount of the surfactant that has not associated with the tissue factor and contaminating proteins, the reagent is thought to control variations in measurements of prothrombin time before and after freeze drying of the reagent.

The tissue factor is thromboplastin, which is also called "factor III of coagulation." The tissue factor includes a naturally derived tissue factor and a recombinant tissue factor. In a reagent according to an embodiment of the present invention, a recombinant tissue factor is preferable because raw materials are easily obtained and stably supplied and because there are small differences in performance between production lots, leading to measurement results superior in reproducibility.

As a naturally derived tissue factor, use can be made, for example, of a tissue factor isolated from the brain, placenta, and others of animals of various species using commonly used procedures. Examples of the species of animals from which a naturally derived tissue factor is isolated include, but are not particularly limited to humans, rabbits, bovines, and monkeys and apes. Among these animals, humans are preferable from the viewpoint of more accurately determining human prothrombin time.

A recombinant tissue factor can be obtained, for example, by expressing the recombinant tissue factor in a transgenic organism carrying a cDNA encoding for a tissue factor of an animal of a desired species. A recombinant tissue factor may be one which is commercially available. Among recombinant tissue factors, a recombinant human tissue factor is preferable from the viewpoint of more accurately determining human prothrombin time. Examples of a cDNA encoding for a tissue factor include, but are not particularly limited to ones which encode for a human tissue factor (GenBank Accession No. NM_001993) and a bovine tissue factor (GenBank Accession No. NM_173878). The transgenic organism is obtained, for example, by introducing into a host organism a vector carrying a cDNA encoding for a tissue factor. Examples of the vector include, but are not particularly limited to baculovirus vectors ABv and BEVS. The vector can be selected as appropriate, depending upon the host to be used. Examples of the host include, but are not particularly limited to silkworm larvae, and insect cells such as Sf9 and Sf 21. Introduction of a vector into a host can be performed by methods in accordance with the type of vector to be used. When the vector is a viral vector, the introduction of a viral vector into a host can be accomplished by infection of the host with a recombinant virus derived from the viral vector. The recombinant tissue factor that has been expressed can be obtained from the transgenic organism, for example, by using the following procedures. First, cells of the transgenic organism are disrupted to prepare a cell lysate. The resulting cell lysate is subjected to centrifugation to give a fraction containing the recombinant tissue factor. Then, the resulting fraction can be solubilized to prepare a solution containing the recombinant tissue factor.

Examples of the surfactant include a nonionic surfactant, an anionic surfactant, a cationic surfactant, and an amphoteric surfactant. Among these surfactants, a nonionic surfactant is preferable because it can more reliably control variations in measurements of prothrombin time before and after freeze drying of the reagent. In the specification, a "surfactant" refers to a compound other than the phospholipid described below.

Examples of the nonionic surfactant include, but are not particularly limited to an alkylglucoside surfactant, an acylalkylglucamine surfactant, an ether surfactant, an ether ester surfactant, and an ester surfactant. These nonionic surfactants may be used alone or as a mixture of two or more surfactants. Among these nonionic surfactants, an alkylglucoside surfactant and an acylalkylglucamine surfactant are preferable form the viewpoint that they can more reliably control variations in measurements of prothrombin time before and after freeze drying of the reagent.

Examples of the alkylglucoside surfactant include, but are not particularly limited to alkylglucoside compounds in which an alkyl group has 6 to 10 carbon atoms. Examples of the alkylglucoside compounds in which an alkyl group has 6 to 10 carbon atoms include, but are not particularly limited to hexyl-β-D-glucopyranoside, heptyl-β-D-glucopyranoside, octyl-β-D-glucopyranoside, nonyl-β-D-glucopyranoside, and decyl-β-D-glucopyranoside. These alkylglucoside surfactants may be used alone or as a mixture of two or more surfactants.

Examples of the acylalkylglucamine surfactant include, but are not particularly limited to alkanoyl methylglucamine compounds in which an alkanoyl group has 7 to 9 carbon atoms. Examples of the alkanoyl methylglucamine compounds in which an alkanoyl group has 7 to 9 carbon atoms include, but are not particularly limited to n-heptanoyl-N-methyl-D-glucamine, n-octanoyl-N-methyl-D-glucamine, n-nonanoyl-N-methyl-D-glucamine, and n-decanoyl-N-methyl-D-glucamine. These acylalkylglucamine surfactants may be used alone or as a mixture of two or more surfactants.

The content of the tissue factor in a reagent according to an embodiment of the present invention is preferably equal to or above $4.0 \times 10^{-5}$ W/V % (0.4 µg/mL), more preferably equal to or above $5.0 \times 10^{-5}$ W/V % (0.5 µg/mL), from the viewpoint that the activity as a reagent for measuring clotting time is ensured, and preferably equal to or below $7.0 \times 10^{-5}$ W/V % (0.7 µg/mL), more preferably equal to or below $6.0 \times 10^{-5}$ W/V % (0.6 µg/mL), from the view point of controlling variations among lots of the reagent.

In a reagent according to an embodiment of the present invention, the value of formula (I) is preferably equal to or above 0.013 µmol/µg, more preferably equal to or above 0.015 µmol/µg, from the view point of controlling variations in clotting time before and after freeze drying of the reagent, and preferably equal to or below 0.05 µmol/µg, more preferably equal to or below 0.025 µmol/µg, from the view point of controlling variations in clotting time before and after freeze drying of the reagent. A reagent according to an embodiment of the present invention contains a tissue factor and a surfactant in such amounts that the value of formula (I) will be 0.013 to 0.05 µmol/µg. Therefore, the use of a reagent according to an embodiment of the present invention controls variations in measurements of prothrombin time before and after freeze drying of the reagent. The content [µmol] of surfactant in a reagent according to an embodiment of the present invention can be determined, for example, by the following formula: {(surfactant concentration in the raw material of tissue factor [W/V %]×10 [g/mL])÷surfactant molecular weight [g/mol]}×(tissue factor concentration in the reagent [µg/mL]/tissue factor concentration in the raw material [µg/mL])×reagent volume [mL]÷$10^6$. The content of total protein in a reagent according to an embodiment of the present invention can be determined by a bicinchoninic acid protein determination assay (BCA method). The raw material of tissue factor is a raw material containing a tissue factor that is used for the production of a reagent for measuring clotting time. The raw material of tissue factor usually further contains a surfactant, in addition to the tissue factor.

A reagent according to an embodiment of the present invention further contains calcium ions. The amount of calcium ions in the reagent can be an amount that is suitable for activating factor VII and allowing the progression of the coagulation reaction. Usually, the amount of calcium ions in the reagent according to an embodiment of the present invention is preferably equal to or above 14 mM, more preferably equal to or above 20 mM, from the viewpoint of preventing influence due to the variations in the concentration of sodium citrate in plasma, and preferably equal to or below 30 mM, more preferably equal to or below 25 mM, from the viewpoint of ensuring the stability of the reagent.

A reagent according to an embodiment of the present invention further contains a phospholipid. The phospholipid facilitates the blood coagulation reaction. The phospholipid is a lipid having a phosphate ester moiety in the molecule. In a reagent according to an embodiment of the present invention, the phospholipid generally forms a liposome having a phospholipid layer. The phospholipid may be a naturally derived phospholipid, or alternatively may be a synthetic phospholipid. Examples of the naturally derived phospholipid include, but are not particularly limited to ones derived from animals such as rabbits, bovines, pigs, chickens, and humans, and plants such as soy beans. Examples of animal-derived phospholipids include, but are not particularly limited to ones derived from rabbit brain, bovine brain, egg yolk, and human placenta. Specific examples of phospholipids include, but are not particularly limited to glycerophospholipids such as a phosphatidylethanolamine compound, a phosphatidylcholine compound, and a phosphatidylserine compound. Examples of the phosphatidylethanolamine compound include, but are not particularly limited to an optionally substituted phosphatidylethanolamine. Examples of the phosphatidylcholine compound include, but are not particularly limited to an optionally substituted phosphatidylcholine. Examples of the phosphatidylserine compound include, but are not particularly limited to an optionally substituted phosphatidylserine. Examples of the substituents of an optionally substituted phosphatidylethanolamine, an optionally substituted phosphatidylcholine, and an optionally substituted phosphatidylserine include, but are not particularly limited to an acyl group having 8 to 20 carbon atoms. Examples of an acyl group having 8 to 20 carbon atoms include, but are not particularly limited to a lauroyl group, a myristoyl group, a palmitoyl group, a stearoyl group, and an oleoyl group. These substituents can be selected as appropriate as long as the blood coagulation reaction is not inhibited.

Examples of the optionally substituted phosphatidylcholine include, but are not particularly limited to phosphatidylcholine, and diacylphosphatidylcholines in which the acyl groups have 8 to 20 carbon atoms, such as dilauroylphosphatidylcholine, dimyristoylphosphatidylcholine, dipalmitoylphosphatidylcholine, distearoylphosphatidylcholine, and dioleoylphosphatidylcholine. Examples of the optionally substituted phosphatidylethanolamine include, but are not particularly limited to phosphatidylethanolamine, and diacylphosphatidylethanolamines in which the acyl groups have 8 to 20 carbon atoms, such as dilauroylphosphatidylethanolamine, dimyristoylphosphatidylethanolamine, dipalmitoylphosphatidylethanolamine, distearoylphosphatidylethanolamine, and dioleoylphosphatidylethanolamine. Examples of the optionally substituted phosphatidylserine include, but are not particularly limited to phosphatidylserine, and diacylphosphatidylserines in which the acyl groups have 8 to 20 carbon atoms, such as dilauroylphosphatidylserine, dimyristoylphosphatidylserine, dipalmitoylphosphatidylserine, distearoylphosphatidylserine, and dioleoylphosphatidylserine. Among these phospholipids, preference is given to phosphatidylethanolamine compounds, phosphatidylcholine compounds, and phosphatidylserine compounds, with dioleoylphosphatidylcholine, dioleoylphosphatidylethanolamine, and dioleoylphosphatidylserine being more preferable, because they allow efficient progression of the blood coagulation reaction. These phospholipids may be used alone or as a mixture of two or more.

The content of the phospholipid in the reagent according to an embodiment of the present invention is preferably equal to or above $5\times10^{-5}$ W/V % (50 µg/mL), more preferably equal to or above $1\times10^{-4}$ W/V % (100 µg/mL), from the viewpoint of ensuring an appropriate normal clotting time and an appropriate ISI (International Sensitivity Index), and preferably equal to or below $2.5\times10^{-4}$ W/V % (250 µg/mL) from the viewpoint of ensuring an appropriate clotting time and an appropriate ISI. The normal clotting time refers to a clotting time of normal plasma.

In a reagent according to an embodiment of the present invention, the tissue factor is associated with the phospholipid layer of a liposome. In the reagent, the phospholipid layer of a liposome is generally thought to be a lipid bilayer. In the reagent, the tissue factor is generally thought to be associated with the phospholipid layer in a state where the tissue factor penetrates through the phospholipid layer.

A reagent according to an embodiment of the present invention may further contain a buffer from the viewpoint of stably maintaining the phospholipid, tissue factor, and calcium ions, which are contained in the reagent. Examples of the buffer include, but are not particularly limited to 4-(2-hydroxyethyl)-1-piperazineethanesulfonic acid (HEPES) buffer and Tris buffer. The pH of the buffer can be in a range of pH that is suitable for stably maintaining the phospholipid, tissue factor, and calcium ions, which are contained in the reagent. The pH of the buffer is preferably equal to or above pH 7.25, more preferably equal to or above pH 7.4, form the viewpoint of stably maintaining the phospholipid and the tissue factor, and preferably equal to or below pH 7.6 form the viewpoint of stably maintaining the phospholipid and the tissue factor. The concentration of buffering component in the buffer is usually in a range in which buffering action is achieved, for example, 25 to 75 mM.

A reagent according to an embodiment of the present invention may further contain auxiliaries. Examples of the auxiliaries include, but are not particularly limited to a preservative, an antioxidant, and an excipient. Examples of the preservative include, but are not particularly limited to sodium azide. Examples of the antioxidant include, but are not particularly limited to butylhydroxyanisole. Examples of the excipient include, but are not particularly limited to alanine, sucrose, and mannitol.

A reagent according to an embodiment of the present invention may be a lyophilizate of the reagent, or may be a solution of a lyophilizate of the reagent dissolved in a solvent.

A reagent according to an embodiment of the present invention may consist of two reagents, or alternatively may consist of one reagent. In cases where a reagent according to an embodiment of the present invention consists of two reagents, the reagent may be composed of, for example, a first reagent containing a tissue factor, a phospholipid, and a surfactant, and a second reagent containing calcium ions. In the first reagent, the tissue factor and the phospholipid are contained therein as associations of the tissue factor and a liposome composed of the phospholipid.

A reagent according to an embodiment of the present invention can be provided as a reagent kit including a container enclosing the reagent. An example of a reagent kit according to an embodiment of the present invention is depicted in FIG. 1. A reagent kit 10 depicted in FIG. 1 includes a container 22 having a reagent 21 according to an embodiment of the present invention placed therein, an attached insert 31, and a box 41. The reagent 21 contains associations 101 of liposomes 200 and a tissue factor 210, a surfactant, which is not depicted, and calcium ions, which are not depicted. The liposome 200 is composed of a phospholipid 201. A phospholipid layer 202 of the liposome 200 is associated with the tissue factor 210 in a state where the tissue factor penetrates through the phospholipid layer. In this embodiment, the reagent kit 10 may include, for example, an aqueous solvent for dilution, control plasma, and others. The aqueous solvent can be selected, as appropriate, from aqueous solvents usually used in clinical tests for blood coagulability. Examples of the aqueous solvent include, but are not particularly limited to water and physiological saline. Examples of the control plasma include, but are not particularly limited to normal plasma. The attached insert 31 includes a description of the procedures for measuring prothrombin time using the reagent kit 10. The box 41 houses the container 22 having the reagent 21 placed therein, and the attached insert 31. The reagent kit depicted in FIG. 1 consists of one reagent 21, but a reagent kit according to an embodiment of the present invention may be a kit in which two reagents are each enclosed within separate containers. In FIG. 1, the phospholipid 201 may be a single phospholipid or a mixture of two or more phospholipids.

2. Method for the Production of a Reagent for Prothrombin Time Measurement

A method according to an embodiment of the present invention for the production of a reagent for prothrombin time measurement (hereinafter also referred to simply as a "reagent production method") includes a step of freeze-drying an aqueous solution containing a tissue factor and a surfactant, wherein the value of formula (I) is 0.013 to 0.05 μmol/μg, thereby to obtain a lyophilizate (this step is hereinafter referred to simply as "step (A)").

Prior to step (A), a tissue factor and a surfactant are mixed in such amounts that the value of formula (I) is 0.013 to 0.05 μmol/μg, thereby to obtain an aqueous solution. The tissue factor and the surfactant are as described above for those that are used in the above-described reagent for prothrombin time measurement. The tissue factor is usually used as an aqueous solution containing the tissue factor mixed with a solvent such as a buffer solution. For the tissue factor-containing aqueous solution, the value of formula (I) is preferably equal to or above 0.013 μmol/μg, more preferably equal to or above 0.015 μmol/μg, from the view point of controlling variations in clotting time before and after freeze drying of the reagent, and preferably equal to or below 0.05 μmol/μg, more preferably equal to or below 0.025 μmol/μg, from the view point of controlling variations in clotting time before and after freeze drying of the reagent.

In the production of the reagent for prothrombin time measurement, the aqueous solution containing a tissue factor and a surfactant usually contains a liposome composed of a phospholipid. In this case, in step (A), a liposome having a phospholipid layer is formed in advance, using the phospholipid. Specifically, a solution of the phospholipid in chloroform is first subjected to evaporation of the chloroform from the solution, thereby to form a phospholipid film. Then, the resulting phospholipid film is swollen in an appropriate buffer to form a liposome having a phospholipid bilayer. This brings about the formation of a solution containing the liposome. The concentration of phospholipid in the liposome-containing solution can be set as appropriate, depending on the use of the reagent. In step (A), the resulting solution containing the liposome may be optionally subjected to an extruder treatment to allow the liposome to have a uniform particle diameter. In such an extruder treatment, a membrane can be used which has an appropriate pore size suitable for obtaining a first liposome with a desired particle diameter. In step (A), the mixed solution of the tissue factor and the surfactant is then mixed with the solution containing the liposome. This brings about a mixed solution of associations of the tissue factor and the liposome, and the surfactant. The phospholipid is as described above for that used in the above-described reagent.

In cases where the reagent for prothrombin time measurement contains calcium ions, the aqueous solution containing the tissue factor and the surfactant contains calcium ions. In these cases, in step (A), a calcium solution is further added to the resulting mixed solution, so as to make an aqueous solution having a desired concentration of calcium ions. Examples of the calcium solution include, but are not particularly limited to an aqueous solution of calcium chloride. The concentration of calcium ions in the calcium solution can be set as appropriate, depending on the use of the reagent.

To the aqueous solution containing the tissue factor and the surfactant may be further added a stabilizing agent and others, if necessary.

In step (A), the aqueous solution is then subjected to freeze drying to make a reagent for prothrombin time measurement.

The reagent production method according to an embodiment of the present invention may further include a step of dissolving the resultant lyophilizate in a solvent. Examples of the solvent include, but are not particularly limited to HEPES buffer, Tris-hydrochloric acid buffer, and purified water. The amount of the lyophilizate to be dissolved in a solvent can be set as appropriate, depending on the use of the reagent.

In the reagent production method according to an embodiment of the present invention described above, freeze drying is performed after a solution containing a tissue factor, a phospholipid, and a surfactant, and a solution containing calcium ions are mixed to obtain a single reagent solution. However, a first reagent solution containing a tissue factor, a phospholipid, and a surfactant, and a second reagent solution containing calcium ions may be separately subjected to freeze drying.

3. Method for Measuring Prothrombin Time

A method for measuring prothrombin time according to an embodiment of the present invention (which is hereinafter referred to simply as a "measurement method") includes steps of: (a) contacting at least the above-described reagent for prothrombin time measurement with a sample of blood, thereby to obtain a measurement sample, and (b) measuring the prothrombin time of the measurement sample.

In an aspect, the measurement method according to an embodiment of the present invention includes steps of: (a1) mixing a reagent for prothrombin time measurement with a sample of blood, thereby to obtain a measurement sample, and (b1) measuring the prothrombin time of the measurement sample. In this case, the reagent is one that contains a tissue factor, a surfactant, a phospholipid, and calcium ions as defined above and in which the value of formula (I) is 0.013 to 0.05 μmol/μg.

In another aspect, the measurement method according to an embodiment of the present invention includes steps of: (a2) mixing a reagent for prothrombin time measurement, a sample of blood, and a calcium salt, thereby to obtain a measurement sample, and (b2) measuring the prothrombin time of the measurement sample. In this case, the reagent is one that contains a tissue factor, a surfactant, and a phospholipid as defined above and in which the value of formula (I) is 0.013 to 0.05 μmol/μg.

In the specification, a "measurement sample" refers to a mixture of at least a sample of blood, a phospholipid, a surfactant, and a calcium salt.

Examples of the sample of blood include, but are not particularly limited to blood, and plasma obtained from blood. In the measurement method according to an embodiment of the present invention, as a sample of blood, plasma obtained from a sample of blood collected from a subject, control plasma, mixtures thereof, and the like can be used. The plasma is obtained, for example, by subjecting a sample of blood to centrifugation so as not to cause hemolysis, thereby removing blood cells. To the sample of blood may be added a known anticoagulant usually used in clinical tests for blood coagulability. Examples of the anticoagulant include, but are not particularly limited to sodium citrate. In the measurement method according to an embodiment of the present invention, as control plasma, normal plasma, plasma for accuracy control, and the like can be used. The normal plasma may be plasma obtained from a sample of blood collected from a healthy individual, or normal plasma which is commercially available.

In step (a), at least a reagent for prothrombin time measurement is contacted with a sample of blood. The temperature at which the reagent and the blood sample are contacted with each other can be a temperature suitable for performing the blood coagulation reaction. The temperature at which the contacting is carried out preferably ranges from 25 to 45° C., more preferably from 35 to 38° C. The period for which the contacting is carried out preferably ranges from 1 to 10 minutes, more preferably from 3 to 5 minutes.

In cases where the reagent for prothrombin time measurement contains a tissue factor, a surfactant, a phospholipid, and calcium ions, the reagent and a sample of blood are contacted with each other in step (a) and, at the same time, the prothrombin time of the measurement sample is determined in step (b). The concentration of calcium ions in the measurement sample is usually 20 to 25 mM. The concentration of phospholipid in the measurement sample is usually 0.45 to 0.55 mM.

On the other hand, in cases where the reagent for prothrombin time measurement contains a tissue factor, a surfactant, and a phospholipid, and does not contain calcium ions, the reagent and a sample of blood are first mixed in step (a). Then, the resulting mixture is brought into contact with a calcium salt. Concomitantly with contacting the mixture with the calcium salt, the prothrombin time of the measurement sample is determined in step (b). In these cases, the amount of the calcium salt to be mixed with the mixture can be an amount that achieves a calcium ion concentration of 20 to 25 mM in the measurement sample.

Prior to step (a), a sample of blood may be warmed to a temperature suitable for the coagulation reaction. The temperature at which a sample of blood is warmed preferably ranges from 30 to 45° C., more preferably from 36 to 38° C.

The prothrombin time of a measurement sample can be determined based on information related to its coagulation. Examples of such information include, but are not particularly limited to changes in the transmitted or scattered light when the measurement sample is subjected to light irradiation, and changes in the viscosity of the measurement sample. In these cases, the prothrombin time of a measurement sample can be determined, for example, by irradiating a measurement sample with light and monitoring the transmitted light which has passed through the measurement sample or the scattered light from the measurement sample, or by monitoring the change in the viscosity of a measurement sample.

In the measurement of prothrombin time, use is made of measurement apparatus which are used for general measurement of prothrombin time. Examples of such measurement apparatus include, but are not particularly limited to blood coagulation measurement apparatus that are commercially available and are equipped with a device for detection of optical information. Specific examples of these measurement apparatus include coagulation analyzers manufactured by SYSMEX CORPORATION under trade names of CS-2000i and CS-2100i.

EXAMPLES

In the following, abbreviations have the following meaning.

<abbreviations>

DOPE: dioleoylphosphatidylethanolamine

DOPC: dioleoylphosphatidylcholine

DOPS: dioleoylphosphatidylserine

HEPES: 4-(2-hydroxyethyl)-1-piperazineethanesulfonic acid

Examples 1 to 5 and Comparative Examples 1 to 5

(1) Preparation of Recombinant Human Tissue Factor

Silkworm larvae were infected with recombinant baculovirus into which cDNA encoding for a human tissue factor (GenBank Accession No. NM_001993) had been incorporated. After seven days from the infection, the expressed protein was extracted from the infected silkworm larvae. The extraction of the expressed protein was carried out in the following procedures. First, the infected silkworm larvae that had been frozen were disrupted in a disruption buffer (having a composition of 150 mM sodium chloride, 10 mM benzamidine, 1 mM phenylmethylsulfonyl fluoride, 1 mM dithiothreitol, 1 mM ethylenediaminetetraacetic acid, 1 mM glycol ether diamine tetraacetic acid, and 20 mM Tris-hydrochloric acid buffer (pH 7.5)). The resulting silkworm disruption material was subjected to centrifugation at 100000×g at 4° C. for 60 minutes to obtain a precipitate fraction. The precipitate fraction was solubilized using extraction buffer A (1 mass % nonyl-β-D-glucopyranoside, 150 mM sodium chloride, and 20 mM Tris-hydrochloric acid buffer (pH 8.0)) or extraction buffer B (1 mass % n-nonanoyl-N-methyl-D-glucamine, 150 mM sodium chloride, and 20 mM Tris-hydrochloric acid buffer (pH 8.0)), to prepare a raw material solution for tissue factor for use in Examples 1 to 5 and Comparative Examples 1 to 5. The concentration of tissue factor in the resulting raw material solution was determined by an ELISA method. The concentration of total protein in the raw material solution was determined by a BCA method. The results are shown in Table 1.

The resulting raw material solution was diluted in buffer A (having a composition of 150 mM sodium chloride and 25 mM HEPES buffer (pH 7.5)), so that the concentration of tissue factor was adjusted to 50 μg/mL to make a tissue factor-containing solution which was used in Examples 1 to 5 and Comparative Examples 1 to 5. The concentration of tissue factor in the resulting tissue factor-containing solution was determined by an ELISA method. The concentration of total protein in the tissue factor-containing solution was determined by a BCA method. The results are shown in Table 1.

TABLE 1

| | Nonionic surfactant | (mass %) | Tissue factor concentration (μg/mL) | Purity (%) | Total protein concentration (μg/mL) |
|---|---|---|---|---|---|
| Comparative Example 1 | Nonyl-β-D-glucopyranoside | 1 | 158.2 | 6.1 | 2593.4 |
| Example 1 | | 1 | 133.0 | 5.5 | 2418.2 |
| Example 2 | | 1 | 184.8 | 13.9 | 1329.5 |
| Example 3 | | 1 | 212.3 | 18.4 | 1153.8 |
| Comparative Example 2 | | 1 | 100.0 | 18.4 | 543.5 |
| Comparative Example 3 | | 1 | 100.0 | 18.4 | 543.5 |
| Comparative Example 4 | n-Nonanoyl-N-methyl-D-glucamine | 1 | 257.1 | 7.4 | 3456.8 |
| Example 4 | | 3.5 | 257.1 | 7.4 | 3456.8 |
| Example 5 | | 5 | 257.1 | 7.4 | 3456.8 |
| Comparative Example 5 | | 6 | 257.1 | 7.4 | 3456.8 |

(2) Preparation of a Liposome-Containing Solution

In a recovery flask, 86.8 mL of a 25 mg/mL DOPC solution in chloroform, 18.6 mL of a 25 mg/mL DOPE solution in chloroform, and 18.6 mL of a 25 mg/mL DOPS solution in chloroform were mixed to prepare a phospholipid-in-chloroform solution. Then, the chloroform was evaporated with rotating the recovery flask containing the phospholipid-in-chloroform solution, using a rotary evaporator. A liposome film was thus formed on the inner surface of the recovery flask. The resulting liposome film was swollen in buffer A to obtain a mixture containing the liposome. Then, the resulting mixture was filtered through a polycarbonate membrane with a pore size of 0.6 μm to make the particle diameter of the liposome particles uniform, thereby obtaining a liposome-containing solution.

(3) Re-constitution of Tissue Factor into a Synthetic Liposome 1550 mL of the liposome-containing solution obtained in (2) was added to 1240 mL of buffer B (having a composition of 12.5 mM calcium chloride, 0.1 g/L butylhydroxyanisole, and 25 mM HEPES buffer (pH 7.5)). The resulting mixed solution was stirred at 37° C. After the mixed solution was ascertained to be sufficiently stirred, to the mixture was added the tissue factor-containing solution obtained in (1). The resulting mixture was stirred at 37° C. During the stirring, a portion of the mixture was collected several times.

To the portion of the mixture that had been collected was added calcium chloride so that the concentration of the calcium chloride was adjusted to 25.0 mM to prepare a reagent for prothrombin time measurement. Then, the contents (amounts) of surfactant and total protein in the reagent were determined. The amount of surfactant was determined using the concentration of tissue factor in the tissue factor-containing solution, by the following formula: {(surfactant concentration in the tissue factor-containing solution [W/V %]×10 [g/mL])÷surfactant molecular weight [g/mol]}×(tissue factor concentration in the reagent [μg/mL]÷tissue factor concentration in the tissue factor-containing solution [μg/mL])×reagent volume [mL]÷$10^6$. The total protein amount was determined by the following formula: {(surfactant concentration in the tissue factor-containing solution [μg/mL]×(tissue factor concentration in the reagent [μg/mL]÷tissue factor concentration in the tissue factor-containing solution [μg/mL])×reagent volume [mL]. Then, the value of formula (I), which is represented by (surfactant amount (μmol)/protein amount (μg)), was calculated. The results are shown in Table 2.

A portion of the resulting reagent was used to measure the prothrombin time for a pool of plasma samples from healthy individuals. A portion of the resulting reagent was placed in a container and subjected to freeze drying. Then, the freeze-dried reagent was re-dissolved in buffer B (in twice the amount before the freeze drying). The reagent that had been dissolved was used to measure the prothrombin time for the pool of plasma samples. In measuring the prothrombin time, use was made of a fully automated coagulation analyzer manufactured by SYSMEX CORPORATION under a trade name of CS-5100. The difference in prothrombin times before and after freeze drying of the reagent was calculated according to formula (II): [difference in prothrombin times before and after freeze drying of the reagent]=[prothrombin time when the reagent that had been subjected to freeze drying was re-dissolved and used]−[prothrombin time when the reagent that had not been subjected to freeze drying was used]. The results are shown in Table 2.

TABLE 2

| | Tissue factor concentration (μg/mL) | Calcium ion concentration (mM) | Total protein amount (μg) | Surfactant amount (μmol) | Value of formula (I) (μmol/μg) | Difference in prothrombin time before and after freeze drying of the reagent (sec) |
|---|---|---|---|---|---|---|
| Comparative Example 1 | 0.50 | 25.0 | 32.8 | 0.4126 | 0.0126 | 1.2 |
| Example 1 | 0.50 | 25.0 | 36.4 | 0.4908 | 0.0135 | −0.4 |
| Example 2 | 0.50 | 25.0 | 14.4 | 0.3532 | 0.0245 | 0.2 |
| Example 3 | 0.50 | 25.0 | 10.9 | 0.3075 | 0.0283 | 0.8 |
| Comparative Example 2 | 0.50 | 25.0 | 10.9 | 0.6527 | 0.0601 | −2.7 |
| Comparative Example 3 | 0.50 | 20.0 | 10.9 | 0.6527 | 0.0601 | −1.9 |
| Comparative Example 4 | 0.50 | 20.0 | 26.9 | 0.2539 | 0.0094 | −5.8 |
| Example 4 | 0.50 | 20.0 | 26.9 | 0.8886 | 0.0330 | −0.8 |
| Example 5 | 0.50 | 20.0 | 26.9 | 1.2694 | 0.0472 | −0.8 |
| Comparative Example 5 | 0.50 | 20.0 | 26.9 | 1.5232 | 0.0566 | −1.6 |

If the difference in prothrombin time before and after freeze drying of the reagent is within one second, then it is considered that the reagent has the performance that is required for measuring the clotting time of actual samples. The results shown in Table 2 have revealed that in the cases of using the reagents for prothrombin time measurement according to Examples 1 to 5, in which the value of formula (I) was 0.0135 to 0.0472 μmol/μg, the difference in prothrombin time before and after freeze drying of the reagent was within one second. Therefore, it has been found that the use of a reagent for prothrombin time measurement which contains a tissue factor and a surfactant and in which the value of formula (I) is 0.013 to 0.05 μmol/μg can control variations in measurements of prothrombin time before and after freeze drying of the reagent.

What is claimed is:

1. A method for measuring prothrombin time, comprising steps of:
    (a) contacting a reagent for prothrombin time measurement with a sample of blood, thereby to obtain a measurement sample, and
    (b) measuring the prothrombin time of the measurement sample, wherein
    the reagent comprises a tissue factor and a surfactant, wherein a value of formula (I), which is represented by (surfactant amount (μmol))/(total protein amount (μg)), is 0.013 to 0.05 μmol/μg.
2. The method according to claim 1, wherein the surfactant is a nonionic surfactant.
3. The method according to claim 2, wherein the nonionic surfactant is an alkylglucoside surfactant or an acylalkylglucamine surfactant.
4. The method according to claim 3, wherein the alkylglucoside surfactant is an alkylglucoside compound in which an alkyl group has 6 to 10 carbon atoms.
5. The method according to claim 3, wherein the acylalkylglucamine surfactant is an alkanoyl methylglucamine compound in which an alkanoyl group has 7 to 9 carbon atoms.
6. The method according to claim 1, wherein the tissue factor is a recombinant tissue factor.
7. The method according to claim 6, wherein the recombinant tissue factor is a recombinant human tissue factor.
8. The method according to claim 1, wherein the reagent further comprises calcium ions.
9. The method according to claim 1, wherein the reagent further comprises a phospholipid.
10. The method according to claim 1, wherein the reagent is a lyophilizate, or a solution of the lyophilizate dissolved in a solvent.

* * * * *